US009872791B2

(12) United States Patent
Ferrigolo et al.

(10) Patent No.: US 9,872,791 B2
(45) Date of Patent: Jan. 23, 2018

(54) ARTICULATED JOINT FOR ORTHOPEDIC ORTHOSES OR BRACES DESIGNED FOR JOINT REHABILITATION (71) Applicant: F.G.P. S.r.l., Dossobuono (IT)

(72) Inventors: Moreno Ferrigolo, Dossobuono (IT); Alberto Turrini, Dossobuono (IT)

(73) Assignee: F.G.P. S.R.L., Dossobuono (IT)

( * ) Notice: Subject to any disclaimer, the term of this patent is extended or adjusted under 35 U.S.C. 154(b) by 265 days.

(21) Appl. No.: 14/439,350

(22) PCT Filed: Sep. 10, 2013

(86) PCT No.: PCT/EP2013/068766
§ 371 (c)(1),
(2) Date: Apr. 29, 2015

(87) PCT Pub. No.: WO2014/067698
PCT Pub. Date: May 8, 2014

(65) Prior Publication Data
US 2015/0290012 A1 Oct. 15, 2015

(30) Foreign Application Priority Data
Oct. 30, 2012 (IT) .............................. VR2012A0215

(51) Int. Cl.
A61F 5/01 (2006.01)
(52) U.S. Cl.
CPC .... A61F 5/0123 (2013.01); A61F 2005/0141 (2013.01); A61F 2005/0148 (2013.01);
(Continued)
(58) Field of Classification Search
CPC .. A61F 5/00; A61F 5/01; A61F 5/0102; A61F 5/0123; A61F 2005/0141;
(Continued)

(56) References Cited

U.S. PATENT DOCUMENTS

| 4,732,143 A | 3/1988 | Kausek et al. |
| 7,320,672 B2 * | 1/2008 | Turrini ................. A61F 5/0123 602/16 |
| 2012/0059296 A1 | 3/2012 | Kompa |

FOREIGN PATENT DOCUMENTS

| WO | 0202035 A1 | 1/2002 |
| WO | 2004078078 A1 | 9/2004 |

OTHER PUBLICATIONS

International Search Authority, Search Report for International Application PCT/EP2013/068766, dated Oct. 7, 2013, European Patent Office, 1 page, The Hague, Netherlands.

* cited by examiner

Primary Examiner — Keri J Nelson
(74) Attorney, Agent, or Firm — Ference & Associates LLC (57) ABSTRACT

An articulated joint for orthopedic orthoses or braces, where the brace comprises rods for the tibia (51) and rods for the femur (52) and an articulated hinge (53) provided with four pivots designed to ensure the necessary mobility obtained by the presence of multiple centres of rotation, and where the articulated hinge (53) comprises two plates (55, 56) reciprocally connected by means of four quadrilaterally positioned hinging means such as rivets (57) or similar, in order to enclose the ends of the rods (51, 52) which face each other, wherein between the ends of the two rods (51, 52) there are spacers or stops (63), and where the outer plate (55) of the articulated hinge (53) presents openings (61, 62) in which are inserted pairs of stops (63) which limit the ROM of the joint.

9 Claims, 14 Drawing Sheets (52) U.S. Cl.
CPC .............. *A61F 2005/0158* (2013.01); *A61F 2005/0165* (2013.01); *A61F 2005/0167* (2013.01)

(58) Field of Classification Search
CPC ...... A61F 2005/0158; A61F 2005/0165; A61F 2005/0167
USPC ....................................... 602/16, 20, 23, 26
See application file for complete search history.

Fig. 22 FLEX 45°

Fig. 23

Fig. 20 FLEX 0° - EXT 0°

ARTICULATED JOINT FOR ORTHOPEDIC ORTHOSES OR BRACES DESIGNED FOR JOINT REHABILITATION

TECHNICAL FIELD

The present invention relates to an articulated joint for orthopedic orthoses or braces designed for the rehabilitation of the joints of the human body such as the knee, the elbow, the ankle, the shoulder and similar.

The present solution provides a brace with features designed to make adjustment of the articulated joint simpler. In general, the present solution also has the objective of improving both the construction and use of the articulated joint so that it is lighter and stronger, simpler to make and easier to use.

At the present time, traditional articulated joints are adjusted by inserting and removing pins. The new joint according to the present invention is, as already stated, designed to make joints simpler, lighter and more cost-effective and does this by using stops of a new design. The stops are inserted inside a seat made in the outer plate against which the counteropposing forces generated by the rods are unloaded.

This invention can be applied in the medical and orthopedic industry and particularly in the production sector of orthopedic braces in general but also of prostheses and braces mainly used in preventative, post-traumatic, rehabilitation and post-operative therapy.

BACKGROUND ART

It is known that people with orthopedic problems of the knee joints and other joints such as the ankle or elbow, require an orthopedic brace or orthoses especially in cases of injury or post-operative trauma. Braces and orthoses provide a hinged constraint between the femur and the tibia or other lever joint parts in order to support stresses which would otherwise be damaging to the human joint itself.

In general, the function of an orthoses is to immobilise or restrict the movement of a joint affected by trauma, arthrosis, sprained ligaments or which have undergone surgery.

Another use of braces is functional rehabilitation or re-education, where the brace can be used to reduce the load on a joint and lessen the pain, or used for preventive purposes in cases of osteoporosis or bone fragility.

Braces usually consist of a rigid or soft framework enclosing the limb and are designed to guarantee adequate harnessing of the joint and prevent the onset of strain on the ligaments and synovial membranes when the injured or convalescent subject is walking.

According to the background art, in the specific case of the knee, the frame of the knee brace comprises means of constraint for the femur and the tibia in areas close to the knee and a structure connecting these means with a jointed hinge positioned at the level of the knee. The means of constraint usually consist of half-rings, fixed with suitable straps, encircling both the femur and the tibia of the injured subject or bands, belts or sleeves made from woven material which create a constraint between the ends of the mechanical joint and the limb.

In an example application of the orthoses to the leg, the mechanical joint is positioned to the side of the femur and tibia. The orthoses has multiple centres of rotation and a configuration with four pivots to faithfully reproduce the kinematics of the human limb.

In order to ensure sufficient freedom of movement for the limb and the correct amount of mobility, the frame is positioned almost entirely along the sides of the joint such as the knee or the elbow.

The presence of four pivots on the joint considerably reduces the risk of the knee brace moving and slipping downwards.

It is also known that each subject needs different degrees of angular freedom depending on the type of injury involved. This is why braces have been developed with means for adjusting and limiting the range of angular freedom.

Traditional joints for knee braces with an adjustable angular range generally comprise a platform fitted with at least one pair of hinge couplings for the respective uprights, fitted with means for restraining the joint in question, in which the platform comprises a central shaped plate and at least one location for an extractable insert which abuts against the plate and at least one end of an upright.

The joint also comprises means of temporary restraint for the inserts with the purpose of limiting the movement of the joint during extension and/or flexion. In order to be able to adjust the range of motion (R.O.M.) in the various possible angular configurations, the insert for limiting flexion and extension must be interchangeable with inserts having different profiles.

The shape of the inserts is such as to limit the reciprocal angular range between the uprights connected to the joint, the shape differing in order to obtain different angular ranges depending on the needs dictated by patient's pathology.

According to the known solutions, the joint presents internal seats for the inserts, consisting of accessible slots formed inside the platform. At the level of each slot, the base surface of the platform presents an opening designed to make the seat of the corresponding insert visible.

While these solutions solve the problems concerning the range of motion (R.O.M.) adjustment system of orthopedic braces with angular range, they do however present other problems which will be described below.

First and foremost, the traditional insert system makes use of components of a relatively large size, creating a first difficulty in the use of the brace due to the considerable thickness of each hinge. The adjustment system is also difficult to use because of the limited stability of the inserts and because of the difficulty in changing the inserts when it is necessary to vary the range.

In general, the traditional joints for orthoses use bulky, heavy components which make them complicated and costly to construct for the manufacturer.

Recently there have been attempts to lighten and simplify orthoses with traditional joints in order to increase their performance. However, they continue to constitute an encumbrance involving practical difficulties for the user due to their excessive weight and size, both factors limiting user comfort.

DESCRIPTION OF THE INVENTION

The present invention provides an articulated joint for orthoses or braces for rehabilitation of the knee or other orthopedic braces, which can be applied as an aid for joints of the human body such as the ankle, the elbow or similar, that is able to eliminate or at least reduce the drawbacks described above.

The present invention also provides a joint for orthoses or orthopedic braces for the rehabilitation of joints where the joint according to the invention is designed overall to be lighter and simpler than traditional braces while maintaining the same strength and versatility.

This is achieved by means of a joint for orthoses or orthopedic braces designed for the rehabilitation of limbs, whose characteristics are described in the main claim.

The dependent claims of the solution in question describe advantageous embodiments of the invention.

The main advantages of this solution concern above all the fact that in general the joint is smaller, lighter, simpler to use and has more compact overall dimensions in comparison with the known solutions and is therefore more comfortable to wear and easier to use for the user.

The joint according to the present invention comprises a system with four points.

The purpose of the rods, made from a light, mouldable material such as aluminium alloy, is to connect the joint mechanism to the limb and vice versa. In the figure provided as an example, the rods have holes of suitable design to make them lighter.

The two plates comprising the joint, an inner and an outer plate, are designed to connect the two rods and are made from a light material such as plastic or aluminium alloy which encapsulates a core of a more resistant material such as stainless steel. The inner part of each plate has two projections which simulate and substitute the function of washers to increase the sliding between the plates.

Located between the ends of the two rods there is a spacer of a suitable size which acts as a stop during flexion and extension.

These stops are made from a light material such as plastic or aluminium alloy and are designed to be placed between the two free ends of the rods and to act as a wedge. They are inserted inside a seat made in the outer plate against which the components of the counteropposing forces generated by the rods are unloaded.

The shape of the rod ends is calculated so that the two counteropposing forces of the rods cancel each other out (in a similar way to a nut cracker) and generate the main parallel and opposing vectors while the residual vectorial components are unloaded onto the external plate.

DESCRIPTION OF THE DRAWINGS

Other features and advantages of the invention will become clear on reading the description given below of one embodiment, provided as a non-binding example, with the help of the accompanying drawings, in which.

DESCRIPTION OF ONE EMBODIMENT OF THE INVENTION

Figure 1:
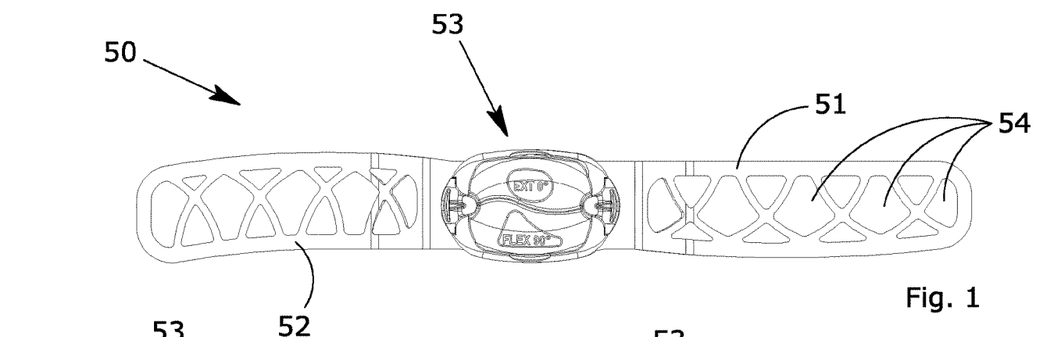
FIGS. 1 to 3 are diagrams showing the joint according to the invention applied to the rods shown respectively at 0° and flexed to 90° and 140°.
Figure 2:
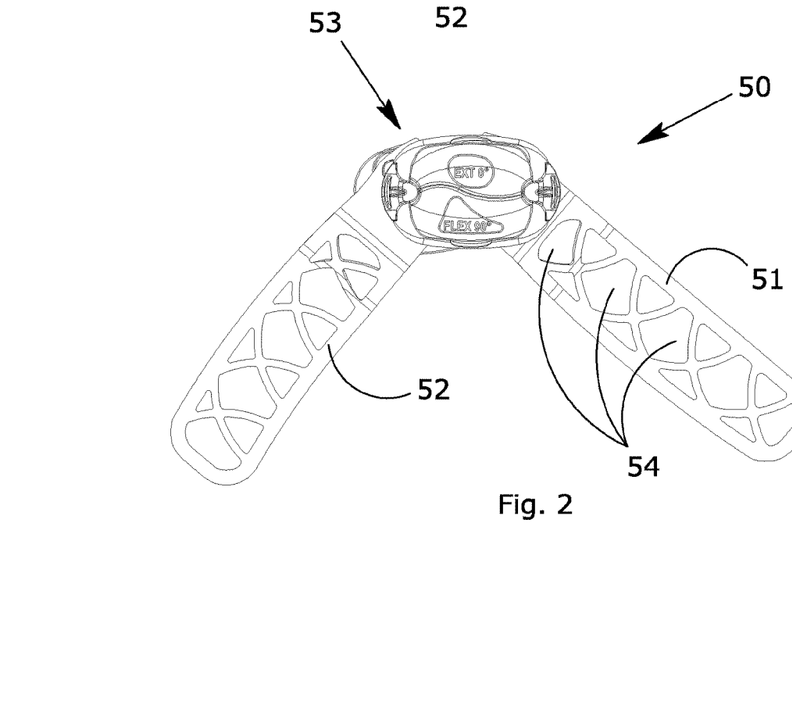
Figure 3:
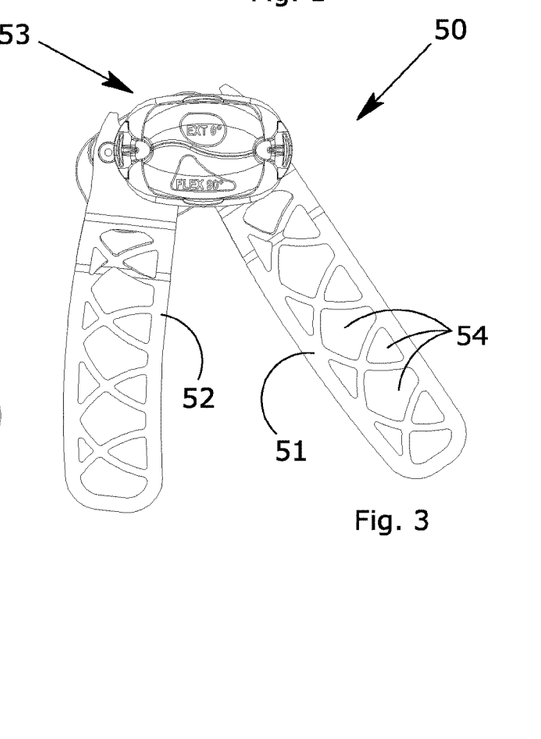
Figure 4:
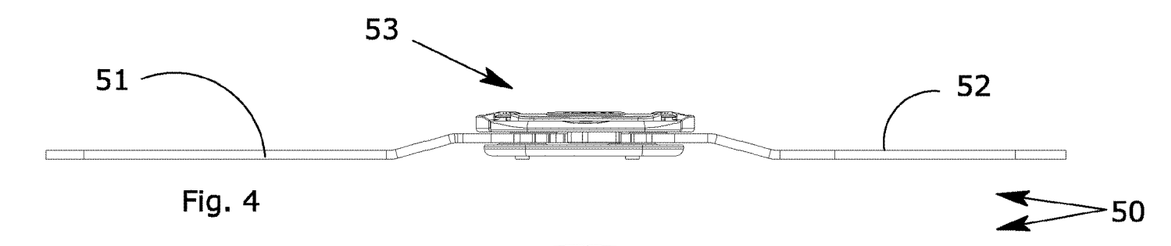
FIGS. 4 to 7 are diagrams showing the joint applied to rods of different shapes.
Figure 5:
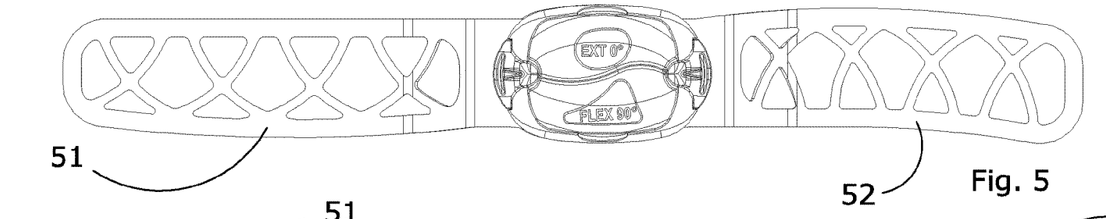
Figures 6, 7:
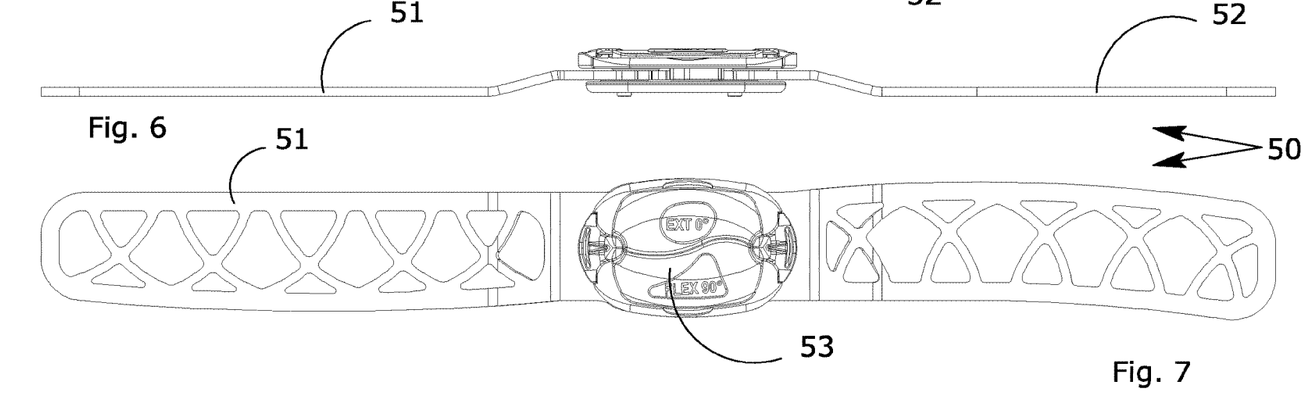

In FIGS. 1 to 3, the numeral 50 indicates in its entirety one of the two groups comprising the joint of an orthoses or an orthopedic brace for the rehabilitation of a limb. The joint comprises means of constraint or rods 51 for the tibia (in the case of application to the knee) and rods 52 for the femur close to the knee and also comprises a structure for connecting these means comprising an articulated hinge 53 located at the knee.

It should be noted that in general everything referring to the knee joint can also be extended to refer to other joints of the human body and these cases are therefore to be considered as coming within the disclosure of this invention.

The tibia rod 51 and the femur rod 52 are positioned to the sides of the tibia and femur respectively and are connected by their joints which form part of the articulated hinge 53. The joints have four pivots providing multiple rotation centres ensuring the required degree of mobility.

A first special feature of the invention is that the rods 51 and 52 are made from a metallic material, preferably aluminium or its alloys, or a high-resistance plastic and have lightening holes 54 and are flexible so that they can be slightly deformed in order to adapt to the shape of the patient's limb.

In the example illustrated, the lightening holes have a design with crossed segments with an arched and/or straight shape and which can also intersect with each other so as to form a metallic mesh which is rigid enough to resist the stresses acting on the uprights fixed to the femur and tibia sector.

The second special feature of the invention is the joint 53 proper itself. It has a lightened and simplified design and construction and is at the same time very strong, strong enough to support high loads when the orthoses is worn by the user.

Figure 8:
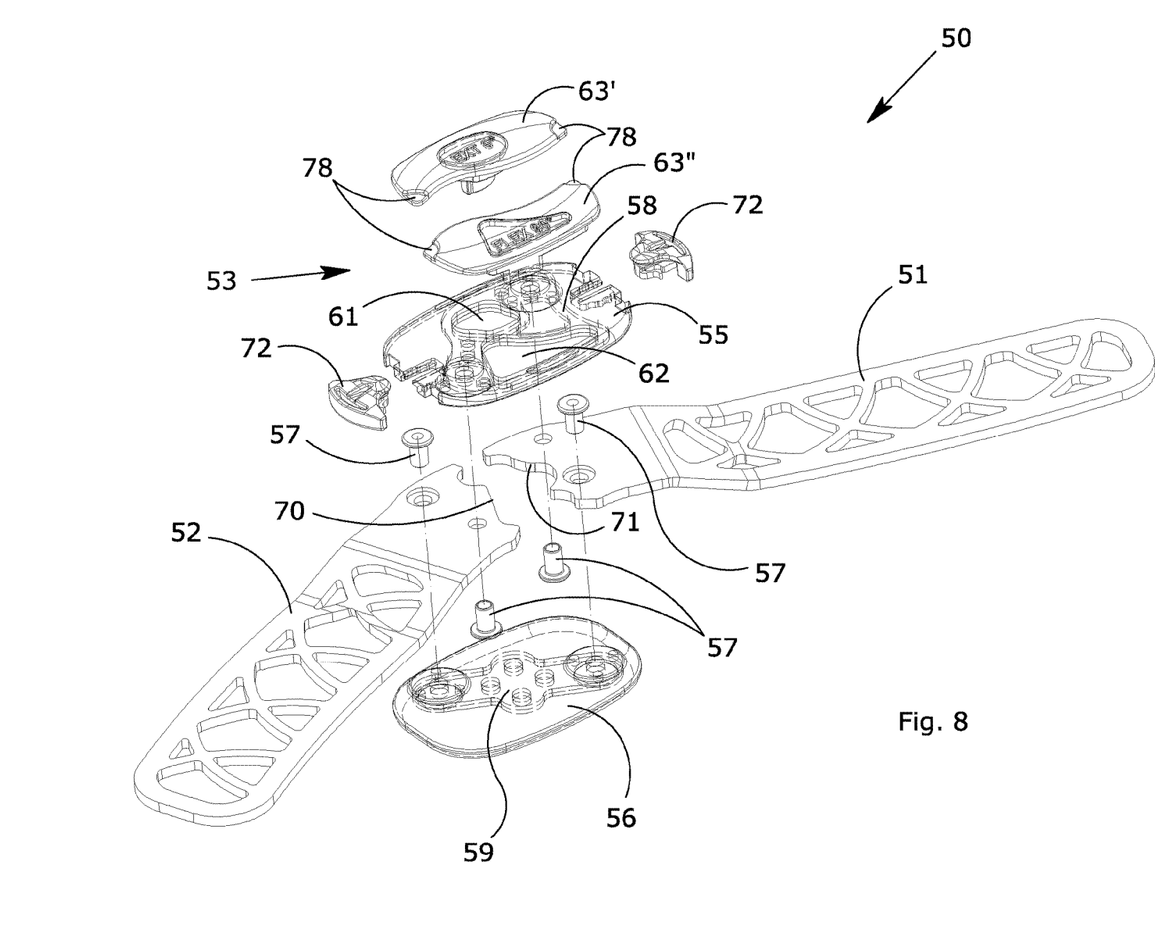
FIG. 8 is an exploded view of the joint according to the invention in general.
Figure 9:
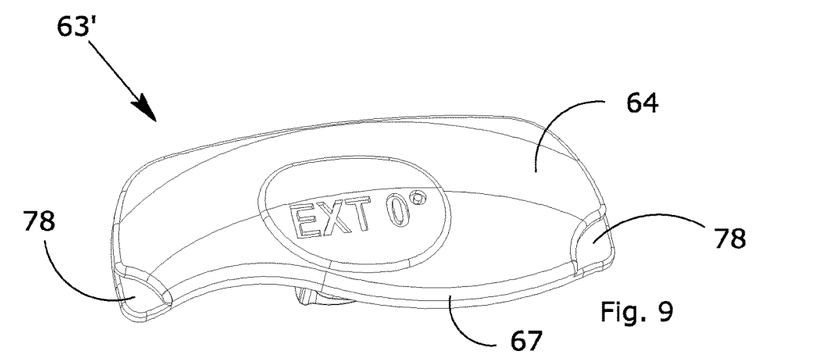
FIGS. 9 and 10 are diagrams indicating respectively the upper and lower parts of an 0° extension stop.
Figure 10:
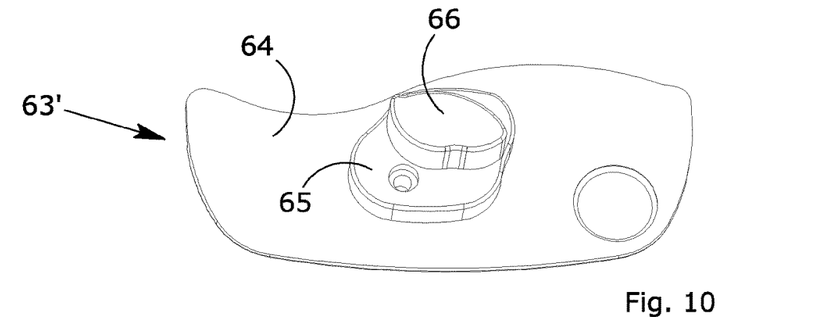
Figure 11:
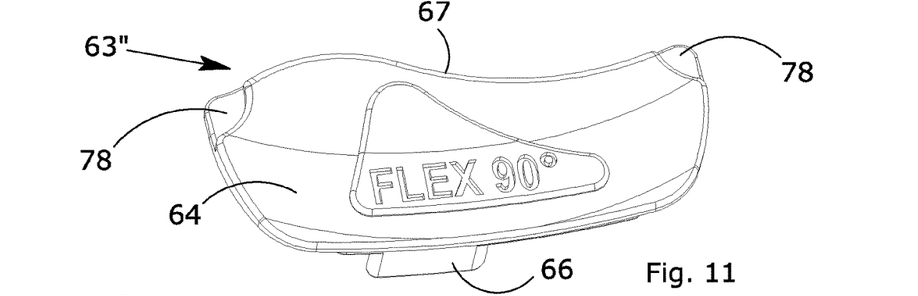
FIGS. 11 and 12 are diagrams indicating respectively the upper and lower parts of an 90° flexion stop.
Figure 12:
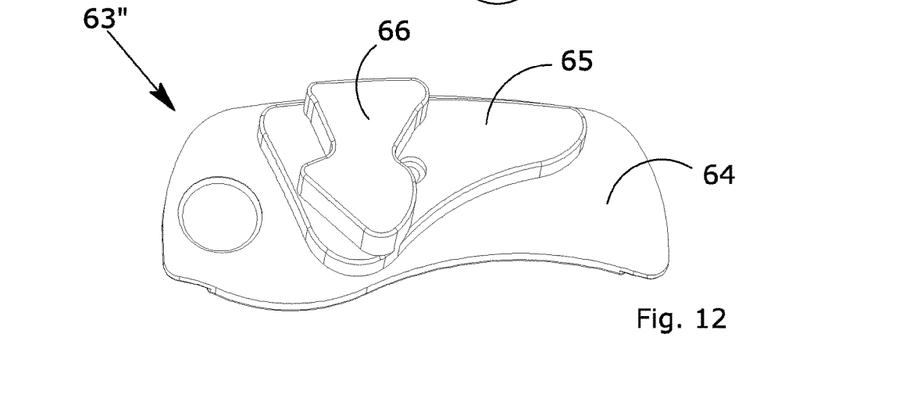

The exploded drawing in FIG. 8 shows that the joint 53 comprises a pair of plates 55 and 56, outer and inner respectively, with a substantially rectangular shape with rounded edges, both having an articulated joint system with four points.

The plates 55 and 56 are held to each other, so as to enclose with the possibility of angular movement the ends of the rods 51 and 52 facing each other, by four rivets 57 which make it possible to maintain a good sliding surface.

The outer plate 55 and the inner plate 56 are made from a plastic material and each plate comprises a reinforcing stainless steel core indicated with 58 for the outer plate 55 and with 59 for the inner plate 56.

The four rivets 57 are closed on the external surface of the stainless steel core thereby avoiding the need to use the traditional stainless steel washers.

The opposite part of the plate has two disc-like projections 60, visible in FIGS. 36 and 37, measuring approximately 0.6 mm which substitute and simulate the action of the sliding washers.

According to the invention, positioned between the ends of the two rods 51 and 52 there are appropriately-sized spacers or stops which act as end stops during flexion and extension of the orthoses rods as described below.

In particular, the external plate 55 of the joint 53 has openings 61 and 62 in which a pair of stops 63 are inserted which limit the range of motion (R.O.M.) according to the operator settings or to the needs dictated by the user's individual situation.

The stops 63, made from plastic material, are inserted in one of the openings 61 and 62 made in the external plate 55 against which the components of the counteropposing forces generated by the rods 51 and 52 are unloaded. This takes into account that the opening 61, which faces towards the front part of the knee, contains the extension stops 63' and is of a smaller size than the opening 62 which is facing towards the rear of the knee and contains the flexion stops 63".

As the Figures from 9 to 12 show in detail, the stops 63 have a particular shape that can be divided into three parts: a first wider outer sector 64 that acts as a cover, a second part 65 that penetrates one of the openings 61 and 62 and is gripped there and a third part 66 that acts as a striker for the ends 70 and 71 of the rods 51 and 52, functioning in a similar way to a nut inserted in a nutcracker.

As a result, the central part 65 has the same conformation for all the stops in extension and in flexion and the shape corresponds to the opening 61 or 62 in which the stops are inserted, while the striker part 66 has a variable shape according to the extension and flexion angles to be set.

In addition, the edges 67 of the two stops facing each other are "S" shaped and during their insertion these edges rest against each other, giving the joint a particular design with a characteristic "S" shaped centre line.

A characteristic feature of the invention is that the stops 63 are inserted transversally on the planar surface 55 of the joint penetrating the openings 61 and 62 so that the projections 66 of the stops 63 act as transverse end stops against the ends 70 and 71 of the rods 51 and 52.

The end parts 70 and 71 of the rods 51 and 52 are appropriately shaped to ensure that the two counteropposing forces of the rods are in opposition to each other, cancelling each other out (in a manner similar to that of a nutcracker) against the third part 66 of each stop, generating parallel and opposite principal vectors. The residual vectorial components are unloaded onto the outer plate 55.

The stops, once inserted in their seats, are held in position by two counteropposing blocks 72 whose task is to hold the stops and prevent them from sliding out without hindrance. The force component to be contrasted is minimal.

Figures 13A, 13B, 13C, 13D, 13E:
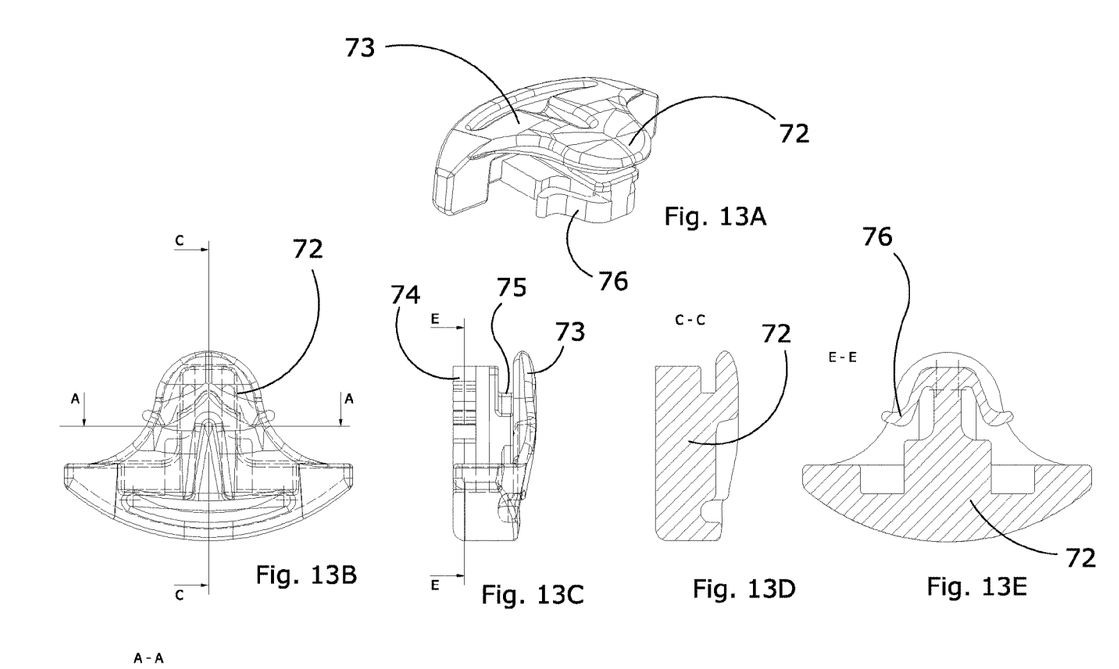
FIGS. 13A to 13F are perspective views and cross sections of a insert block designed to block the stops.
Figure 13F:
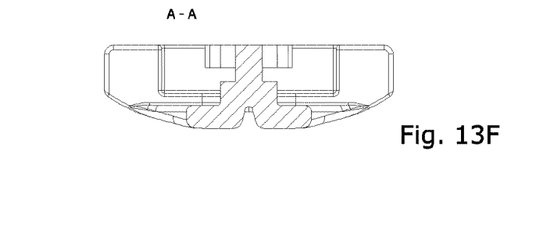
Figure 14:
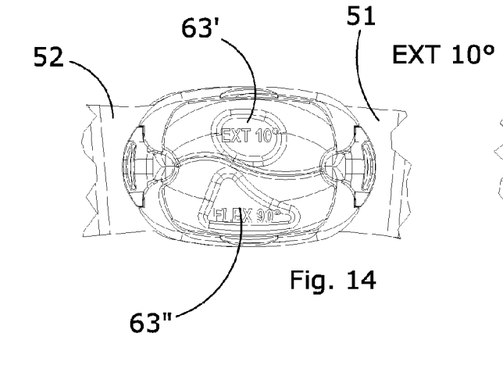
FIGS. 14 to 19 are pairs of diagrams showing respectively front views and cross sections of the joint locked in the extension position at 10°, 20° and 30°.
Figure 15:
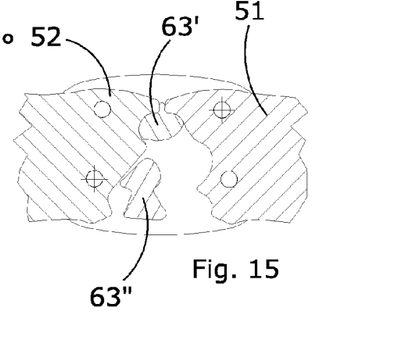
Figure 16:
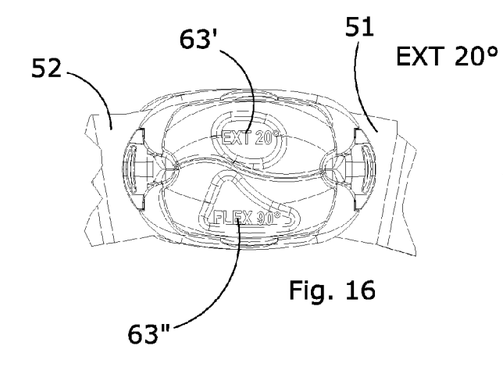
Figure 17:
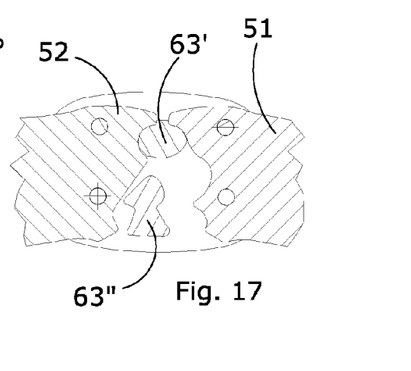
Figure 18:
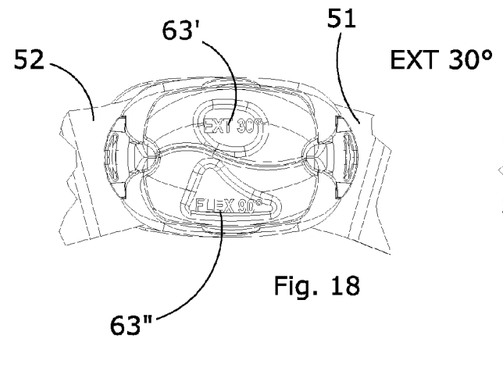
Figure 19:
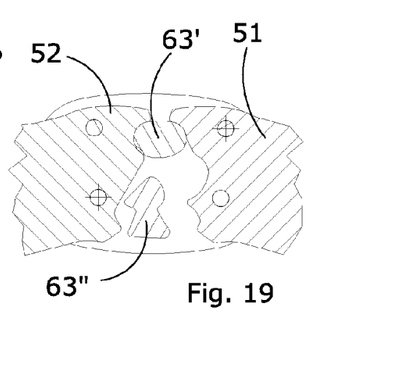
Figure 20:
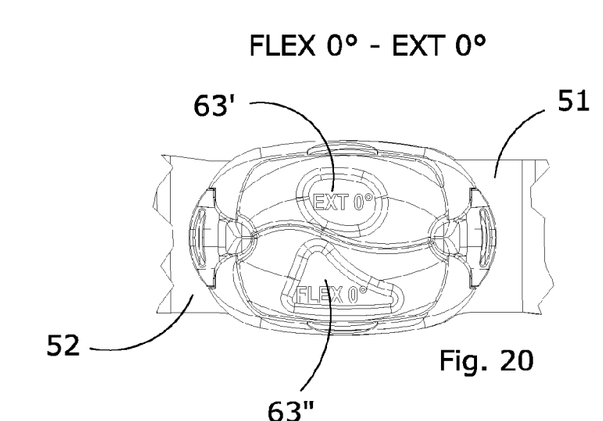
FIGS. 20 to 27 are pairs of diagrams showing respectively front views and cross sections of the joint locked in the flexion position at 0°, 45°, 90° and 140°.
Figure 21:
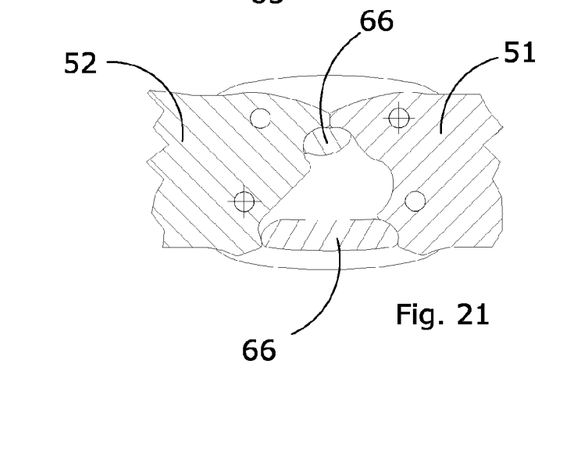
Figure 22:
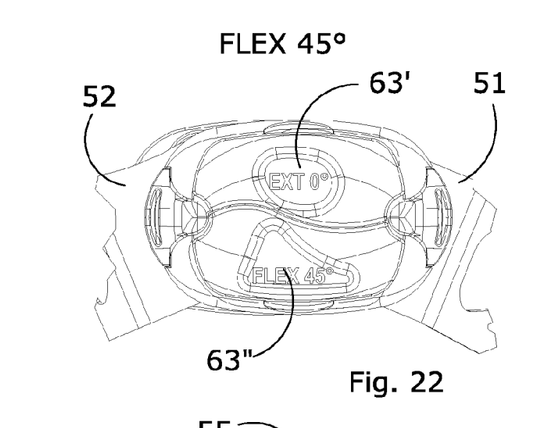
Figure 23:
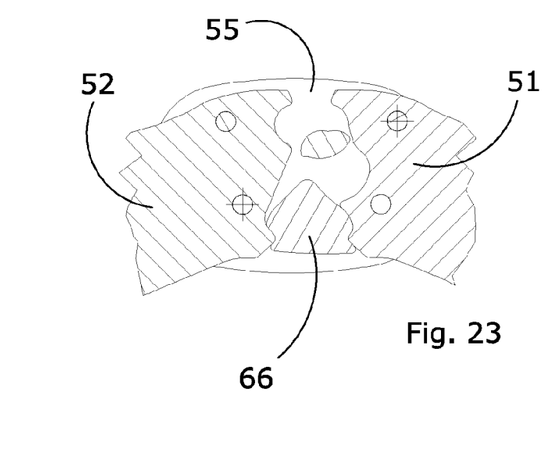
Figure 24:
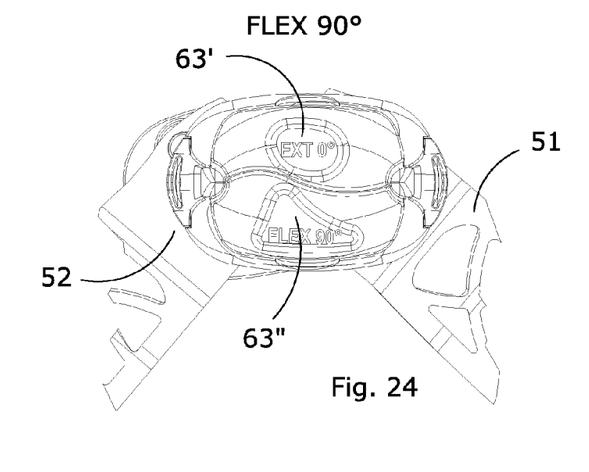
Figure 25:
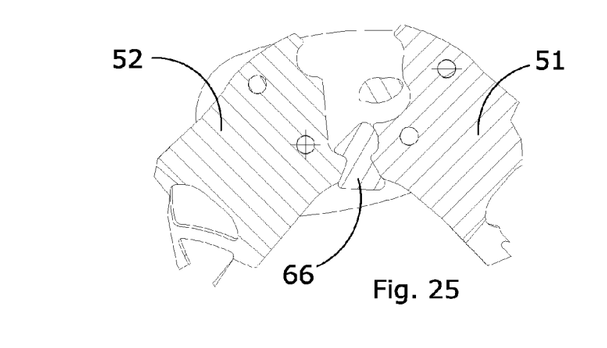
Figure 26:
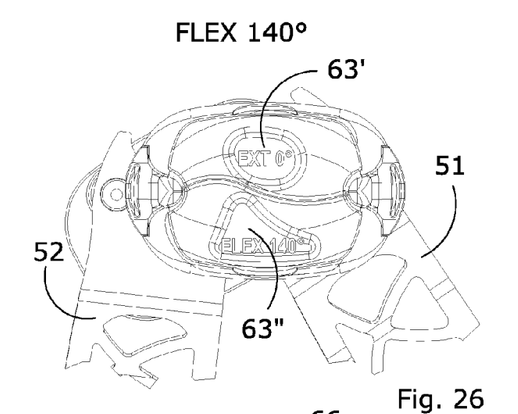
Figure 27:
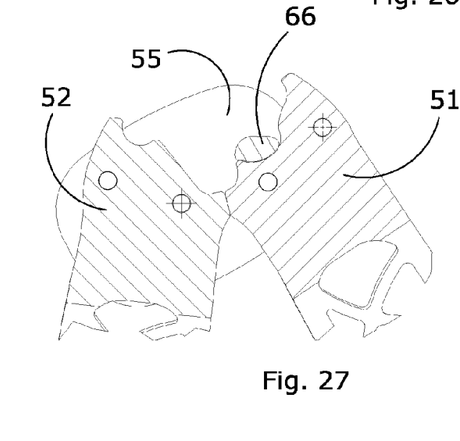
Figure 28:
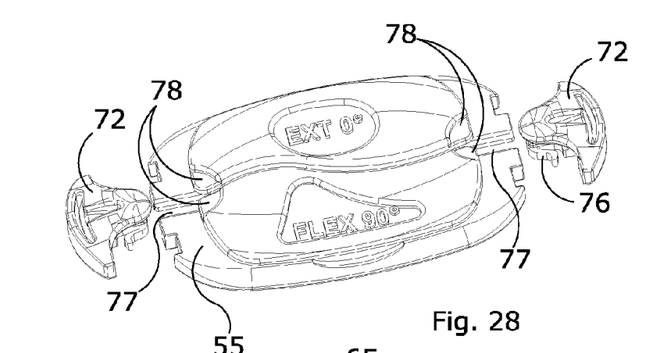
FIGS. 28 and 29 are diagrams showing the joint viewed from above and below, without the rods and fitted with the stops positioned and the blocks before insertion.
Figure 29:
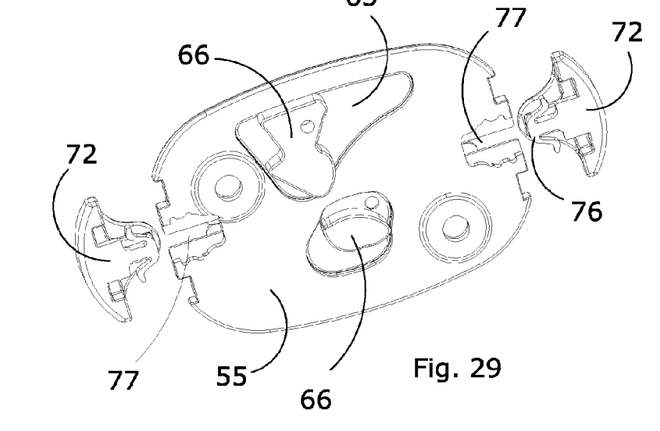
Figure 30:
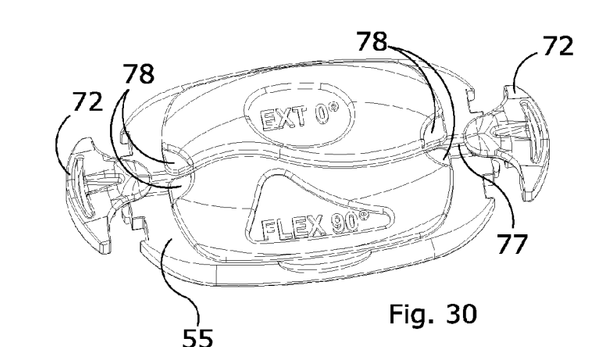
FIGS. 30 and 31 are diagrams showing the joint viewed from above and below, without the rods and fitted with the stops positioned and the blocks also positioned before insertion.
Figure 31:
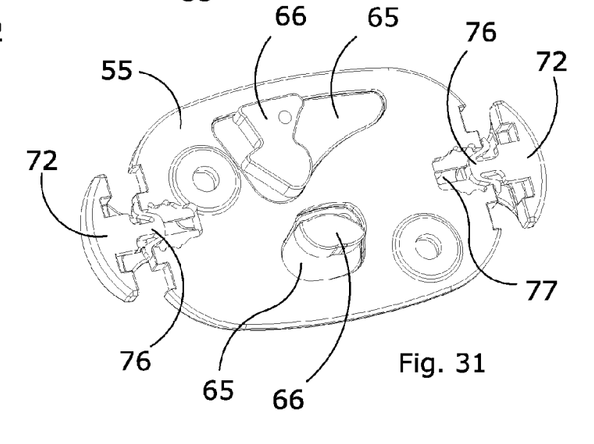
Figure 32:
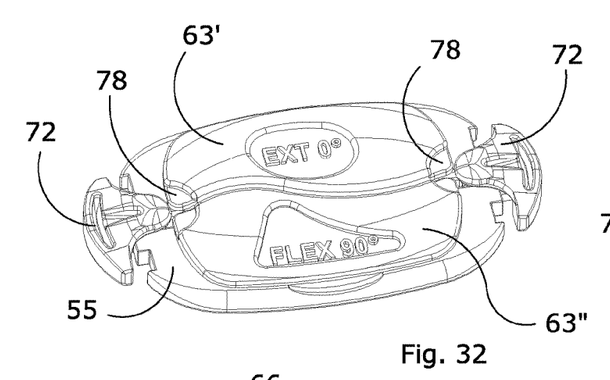
FIGS. 32 and 33 are diagrams showing the joint with the stops positioned and where the blocks can no longer be removed, that is, in the open position for removing the stop.
Figure 33:
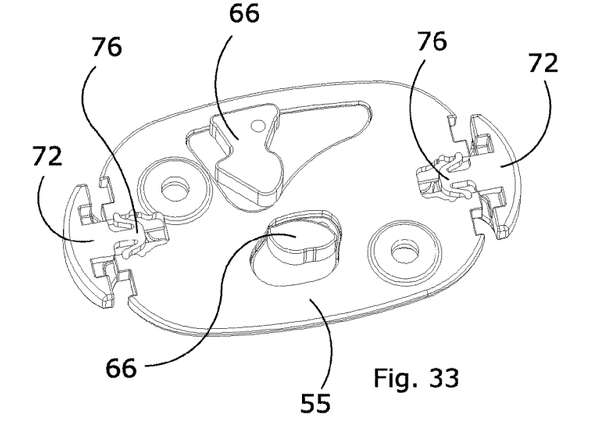
Figure 34:
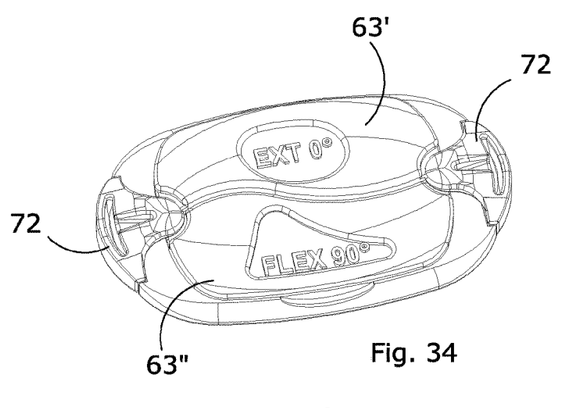
FIGS. 34 and 35 are diagrams showing the joint with the stops positioned and the blocks fully inserted and in the stop blocking position.
Figure 35:
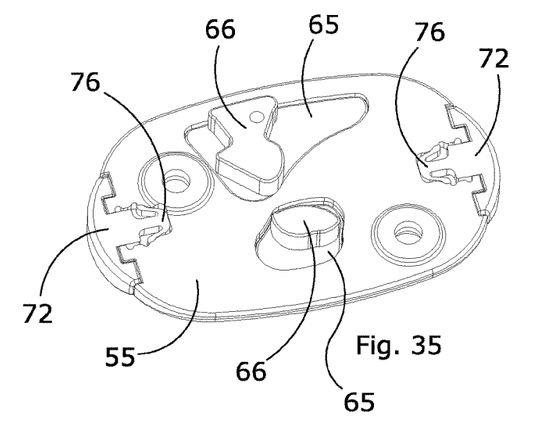
Figure 36A:
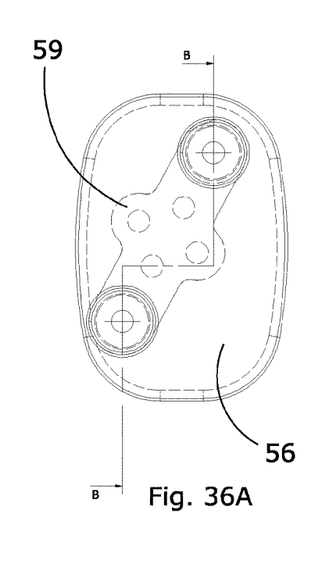
FIGS. 36A to 36G are detailed diagrams of the right-hand side internal plate of the joint according to the present invention considering that the left-hand side internal plate is a mirror image of this.
Figure 36B:
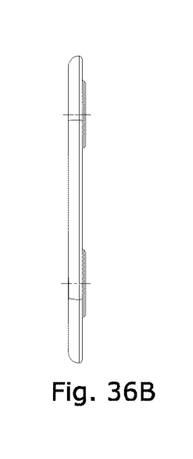
Figure 36C:
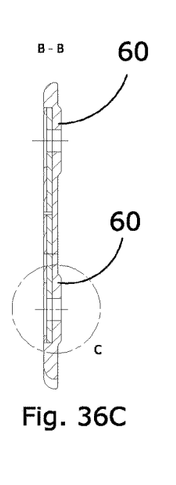
Figures 36D, 36G:
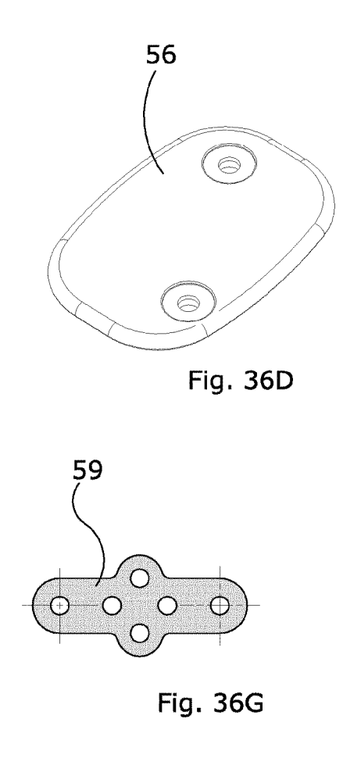
Figure 36E:
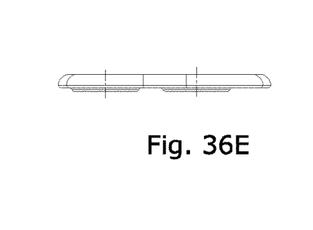
Figure 36F:
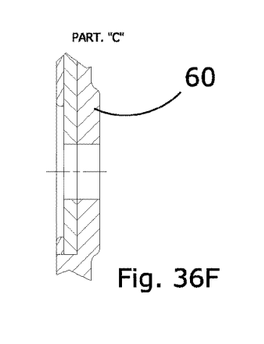
Figure 37A:
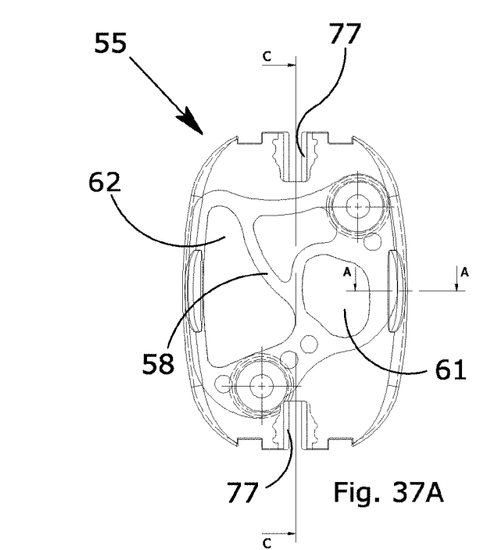
FIGS. 37A to 37H are detailed diagrams of the right-hand side external plate of the joint according to the present invention considering that the left-hand side external plate is a mirror image of this.
Figures 37B, 37C:
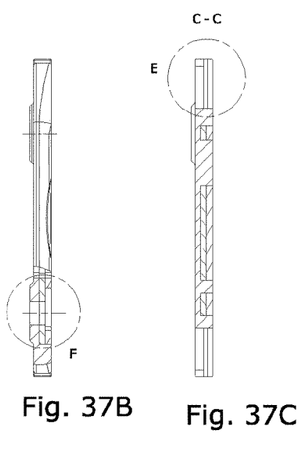
Figure 37D:
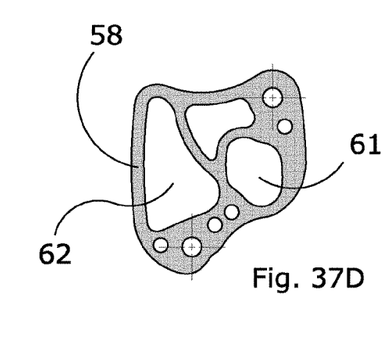
Figure 37E:
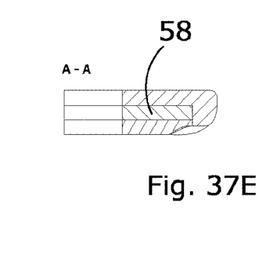
Figure 37F:
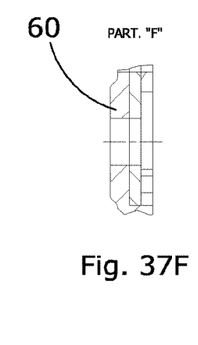
Figure 37G:
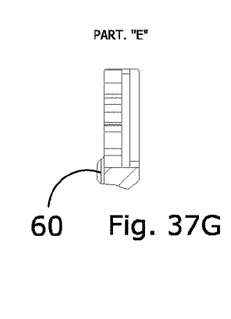
Figure 37H:
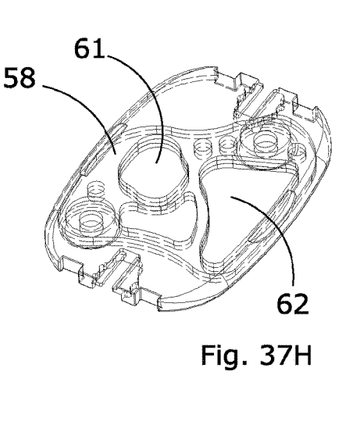

As FIG. 13 shows in detail, the counteropposing blocks 72 comprise an outer element 73 and an inner element 74 with a hollow housing 75 between them. In addition, the blocks 72 comprise an elastic stop anchor fork (76) that partially or totally holds the blocks in position.

The Figures from 28 to 35 show that the blocks 72 are inserted in hollow housings 77 in the two opposite longitudinal ends of the plate 55 of the joint, so that the outer element 73 goes over the lowered parts 78 present on the two opposite corners of each stop 63 thus gripping the adjacent pairs of lowered parts 78 of the two stops facing each other; this is shown in the figures from 28 to 35.

The elastic stop anchor fork 76 which causes the partial and total gripping of the blocks functions as shown in FIGS. 29, 31, 33 and 35, that is, the two elastic ends of the anchor 76 operate inside a lowered shaped part of the housing 77, which presents pairs of opposite notches that define at least two positions that can be reached by the blocks, a first position in which the blocks cannot be withdrawn, that is to say in the open position to withdraw the stops, and a second position in which the blocks are fully inserted and in the stop blocking position.

A further function of the stops 63 is to act as a cap for the joint given that the external sectors 64 completely cover the joint and cover the mechanism with an oval shaped cover divided into the two halves of the "S" shape thereby further improving the design and appearance of the joint.

In order to form the rounded shapes, the inner and outer plates, the stops 63 and the end stop blocks 72 are made from round section profile. The rounded shape formed in this way is ergonomic, has a pleasing appearance and does not have any sharp edges which might catch on and damage fabric.

FIG. 8 shows that the articulated quadrilateral comprises two rods 51 and 52 connected to the two plates 55 and 56 by the four rivets 57.

The extension stop 63' and the flexion stop 63" are always inserted in the outer plate 55. The EXT 0° and FLEX 140° stops are inserted to obtain the maximum angle of flexion between the rods, in other words, in conditions where no limitation to the angle of the joint is required.

Figure 38A:
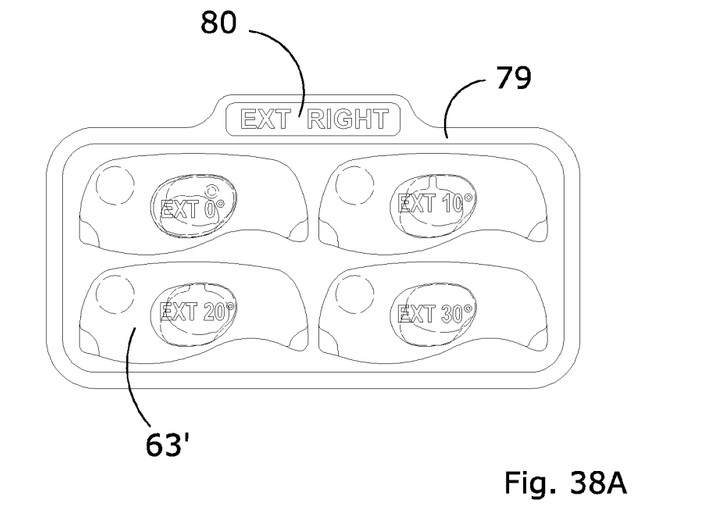
FIGS. 38A and 38B are diagrams showing a series of stops for extension precut on an external frame and to be inserted where required in the joint according to the invention.
Figure 38B:
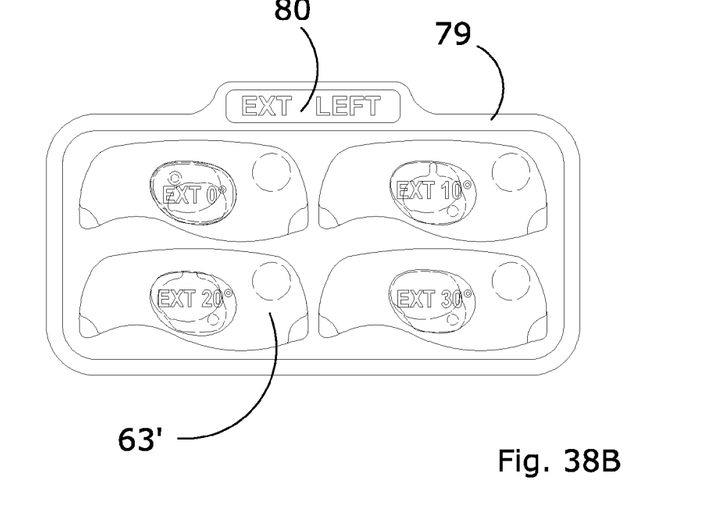
Figure 39A:
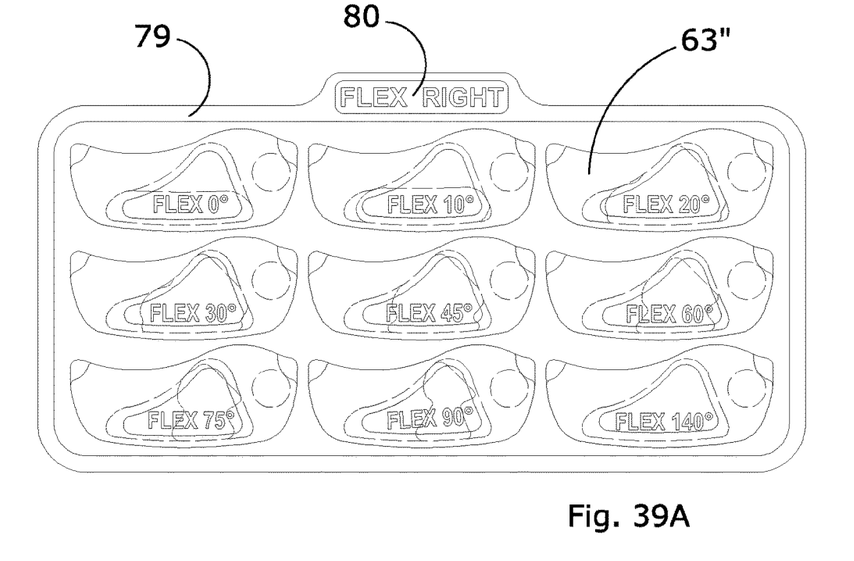
FIGS. 39A and 39B are diagrams showing a series of stops for flexion pre-cut on an external frame and to be inserted where required in the joint according to the invention.
Figure 39B:
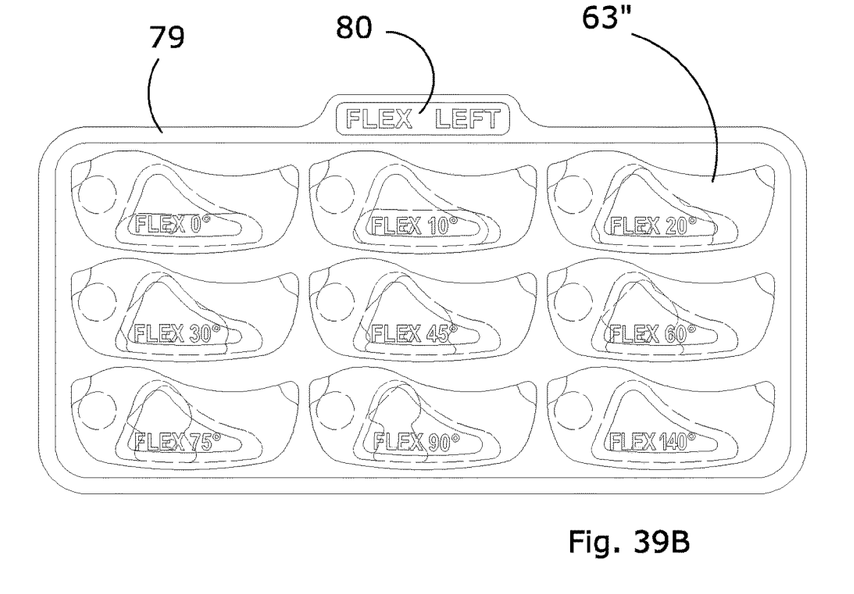

FIGS. 38 and 39 indicate a solution where the stops are grouped together in sets in storage holders 79 which forms a type of storage frame to which the stops are temporarily attached to pre-cut connectors and from which they can easily be detached when required for use.

The upper part of the storage holders 79 have reference tabs 80 indicating the set of stops contained in the storage holders. The sets are for Extension Right and Extension Left (FIG. 38) and for Flexion Right and Flexion Left (FIG. 39).

The invention as described above refers to a preferred embodiment. It is nevertheless clear that the invention is susceptible to numerous variations which lie within the scope of its disclosure, in the framework of technical equivalents.

The invention claimed is:

1. An articulated joint for orthopedic orthoses or braces designed for joint rehabilitation forming part of each of two groups which make up the frame of an orthopedic orthosis or brace designed for joint rehabilitation, said brace comprising a means for knee constraint consisting of rods for the tibia and rods for the femur configured to be positioned in areas proximal to the joint and of a structure connecting said means comprising an articulated hinge configured to be positioned at the level of the joint itself and provided with four pivots designed to ensure the necessary mobility obtained by the presence of multiple centres of rotation, said articulated hinge comprising two plates reciprocally connected by means of four quadrilaterally positioned hinging rivets in order to enclose the ends of the rods which face each other, wherein between the ends of the rods there are stops limiting the flexion and extension movements of the rods, and wherein an outer plate of the two plates of the articulated hinge includes openings which accommodate pairs of stops which limit the range of motion (R.O.M.) of the joint, said stops being located transverse with respect to the planar surface of the articulated hinge, penetrating the openings, so that projections of the stops act as transverse stops against the ends of the rods.

2. The articulated joint of claim 1, wherein once inserted in the openings of the articulated hinge, said stops are held in position by two opposite blocks consisting of an outer element and an inner element with a hollow housing between them, said blocks comprising an elastic stop anchor fork that causes the partial and total gripping of the blocks in combination with a shaped housing of the plate.

3. The articulated joint of claim 2, said two opposite blocks being located in hollow housings in the two opposite longitudinal ends of the plate of the joint, so that an outer element surmounts lowered parts present on the two opposite corners of each stop, gripping adjacent pairs of lowered parts of two stops facing each other, and wherein two elastic ends of the anchor operate inside a lowered shaped part of the housing, which presents pairs of opposite notches that determine at least two positions that can be reached by the blocks, a first position in which the blocks cannot be withdrawn, wherein the first position is associated with an open position where the stops can be removed, and a second position in which the blocks are fully inserted and in a stop blocking position.

4. The articulated joint of claim 2, said two opposite blocks being located in hollow housings in the two opposite longitudinal ends of the plate of the joint, so that the outer element surmounts lowered parts present on the two opposite corners of each stop, gripping adjacent pairs of lowered parts of two stops facing each other.

5. The articulated joint according to claim 4, said elastic stop anchor fork being made in such a way that the two elastic ends of the anchor operate inside a lowered shaped part of the housing, which includes pairs of opposite notches that determine at least two positions that can be reached by the blocks, namely a first position in which the blocks cannot be withdrawn, wherein the first position is associated with an open position where the stops can be removed, and a second position in which the blocks are fully inserted and in a stop blocking position.

6. The articulated joint of claim 1, wherein each stop comprises a first wider outer part acting as a cover, a second part that penetrates one of the openings and is gripped therein, and a third part acting as a striker for the ends of the rods, and wherein the second part presents the same conformation for all the stops in extension and in flexion and the shape corresponds to the opening in which the stops are inserted, while the third part has a variable shape according to the extension and flexion angles to be set.

7. The articulated joint of claim 1, wherein edges of the pairs of stops facing each other are "S" shaped and during their insertion these edges rest against each other.

8. The articulated joint of claim 1, wherein the end parts of the rods have an appropriate shape made in such a way that the forces of the rods are in opposition to each other, reciprocally cancelling each other against the third part of each stop, which acts as a striker, and generating parallel and opposite principal vectors.

9. The articulated joint of claim 1, wherein the rods are made from a material selected from the group consisting of aluminium, aluminium alloy, and high resistance plastic, and wherein the rods are provided with lightening holes and have plastic features so that they can be slightly deformed in order to adapt to the shape of the patient's limb.

* * * * *